United States Patent [19]

Streczyn et al.

[11] 4,278,970
[45] Jul. 14, 1981

[54] ALARM CIRCUIT FOR DETECTING OVERHEATED CONDITION

[76] Inventors: Michael Streczyn, 1218 Junipero, Redwood City, Calif. 94061; Joseph B. Loughlin, 20701 Beach Blvd., Space 231, Huntington Beach, Calif. 92648

[21] Appl. No.: 35,321

[22] Filed: May 2, 1979

[51] Int. Cl.³ .................... G08B 17/06; G08B 21/00
[52] U.S. Cl. .................... 340/599; 128/736; 73/362 AR; 337/298; 340/573; 340/635
[58] Field of Search ............... 340/599, 573, 598, 664, 340/584, 595, 635; 307/117, 257; 337/298, 14; 73/362 SC, 362 AR; 128/736

[56] References Cited

U.S. PATENT DOCUMENTS

| | | | |
|---|---|---|---|
| 3,420,104 | 1/1969 | Troemel et al. | 73/362 SC |
| 3,494,196 | 2/1970 | Moussette | 340/573 |
| 3,671,953 | 6/1972 | Goldberg | 340/595 |
| 3,680,384 | 8/1972 | Grindheim | 73/362 AR |
| 3,748,655 | 7/1973 | Engelhardt et al. | 340/635 |
| 3,960,138 | 6/1976 | Doss et al. | 340/573 |
| 4,003,038 | 1/1977 | Meijer | 340/598 |

Primary Examiner—Glen R. Swann, III
Attorney, Agent, or Firm—Willie Krawitz

[57] ABSTRACT

An alarm circuit for detection of an overheated condition comprises a bridge rectifier or a battery to provide a d.c. input, and a detector bridge including a thermistor and Zener diode in adjacent arms. The diode is set to operate along that portion of the thermistor response curve which is slowly changing. Hence, the Zener diode will be activated if the thermistor detects at the very onset of an overheated condition. Bridge unbalance is fed to an operational amplifier which activates a transistor to turn on an alarm such as an audio indicator, LED, telemetry system, etc. The alarm circuit has application for detection of a line overload, as a monitoring device for patients and for persons undergoing physical activity such as joggers and the like. By sounding an early alarm, overheating in a line wire caused by say, an overheated appliance, can be corrected with a consequent energy saving and minimizing damage to the appliance.

11 Claims, 3 Drawing Figures

ALARM CIRCUIT FOR DETECTING OVERHEATED CONDITION

BACKGROUND OF THE INVENTION

This invention relates to a new and improved circuit for detecting temperature changes such as overheating in a line wire, changes in skin temperature of an individual, etc. The circuit is particularly useful in detecting a temperature increase over that portion of a thermistor detection curve which is changing slowly in the area of interest, i.e., about 300° K.–400° K. By adapting the circuit to detect these relatively small changes, it is easier to provide a warning before the thermistor detection curve begins to move in a steep upward incline where it is difficult to sound an alarm at a specific point.

Widely differing types of circuit overloading or an overheating condition can be detected quickly and accurately. One type of an overheated condition is produced by the overloading of an extension cord or electrical device. It would be preferred to detect the onset of this overheated condition rather than wait for a marked temperature rise or runaway overheating before sounding an alarm. Also, many extension cords of say, 18 gauge have a capacity of about 5–10 amps and they can burn out before a circuit breaker operating at 15 amps will detect this condition. Furthermore, for each 10° C. rise in temperature, a doubling in chemical reaction rates, such as in a line wire burn, will occur. Hence, even if a circuit breaker reacts in time, considerable energy loss and line wire decomposition can occur.

Another type of an overheated condition is caused by failure of a person undergoing physical activity to perspire adequately when performing physical exercise such as calisthenics, cycling, swimming, jogging, etc. Failure to perspire effectively might indicate a person's heat dissipating mechanism has become impaired, thereby causing an internal heat build up, or the individual has become dehydrated, etc. This condition can be accompanied by a decrease of evaporative losses and a sudden rise in skin temperature which reflects central body temperature. If the individual were made aware of this sudden temperature rise, activity could be ceased before a potentially dangerous body condition became aggravated; also, remedial steps could be taken, such as lowering the activity rate, resting, cooling off, taking oxygen, drinking fluids, etc. In the case of a patient, a sudden temperature increase might indicate some type of emergency treatment was necessary.

In certain instances, the heartbeat of a person undergoing exercise may accelerate, and this would alert the individual to slow down activity. However, in other cases, heart stroke volume increases, and this can pose a danger because the person undergoing exercise does not realize the heart function has increased, and the exercise is continued rather than being slowed down. Examples of heat intolerant individuals are reported in "Body Fluid Response of Heat-Tolerant and Intolerant Men To Work In a Hot Wet Environment", Journal of Applied Physiology, Vol. 40, No. 1, Jan. 1976, by L. C. Senay and R. Kok.

THE INVENTION

According to the invention, a circuit is provided for detecting an overload or overheating condition which comprises a d.c. powered detection bridge circuit containing a thermistor in one arm and a Zener diode in an adjacent arm, the bridge being adjusted for thermistor changes in the 300° K.–400° K. range of the bridge, whereby thermistor changes in this range, indicating a circuit overload or excessive heating, will unbalance the bridge sufficiently causing the Zener diode to send a signal for amplification to activate an alarm circuit. If necessary, a second thermistor may be utilized in place of the Zener diode for detection of bridge unbalance at high temperature conditions. However, use of a Zener diode is preferred due to its lower cost and because it can be incorporated into a chip, which is more desireable at the end of an extension cord, in a medical device, etc.

Figures 1, 2:
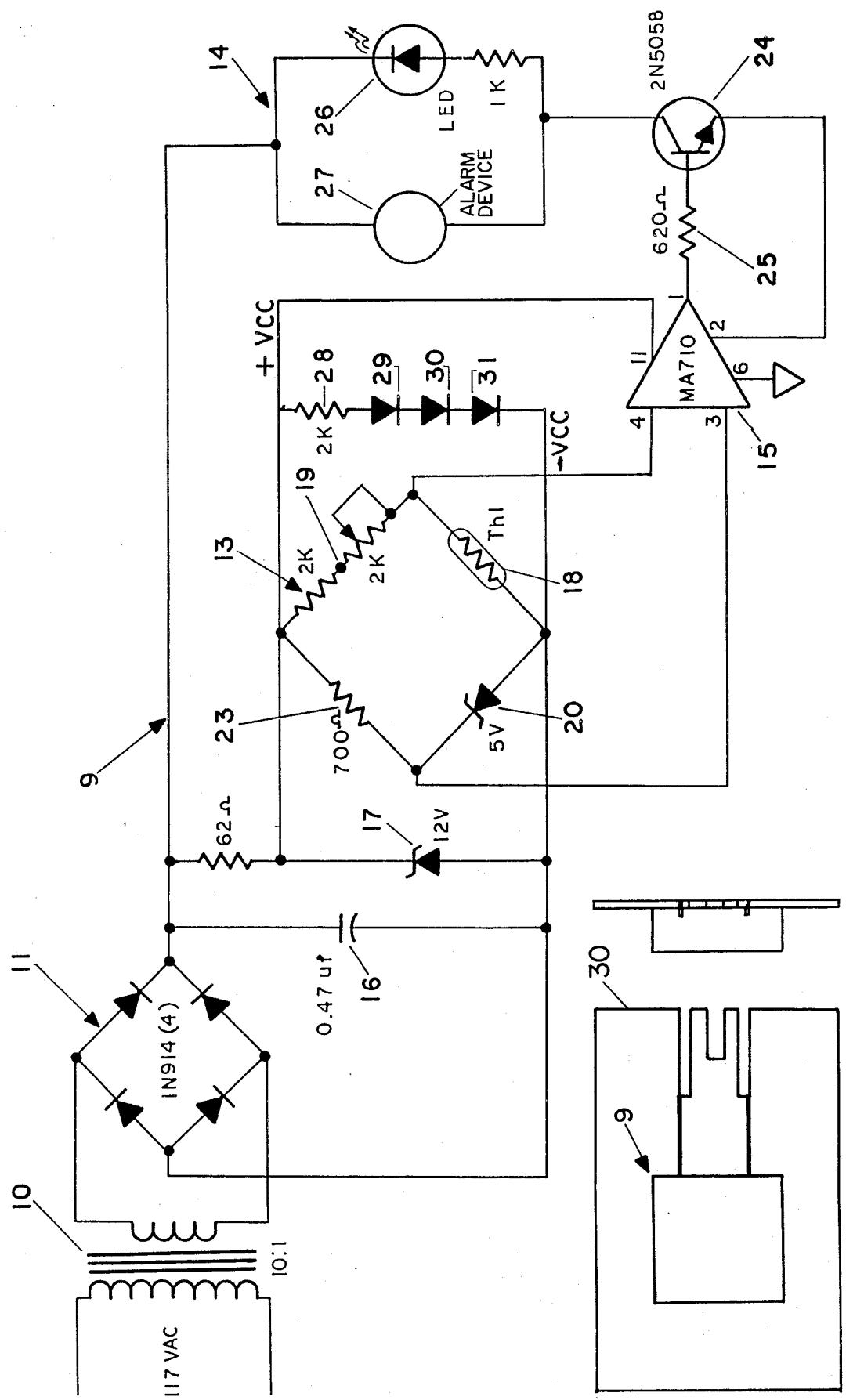
FIG. 1 is a diagram showing a detection circuit of this invention adapted for use with an A.C. line.
FIG. 2 is a plan view of one type of circuit board for use with the detection and alarm circuit which may be conveniently plugged into a line wire; and, FIG. 3 is a circuit diagram showing another embodiment of this invention.
Figure 3:
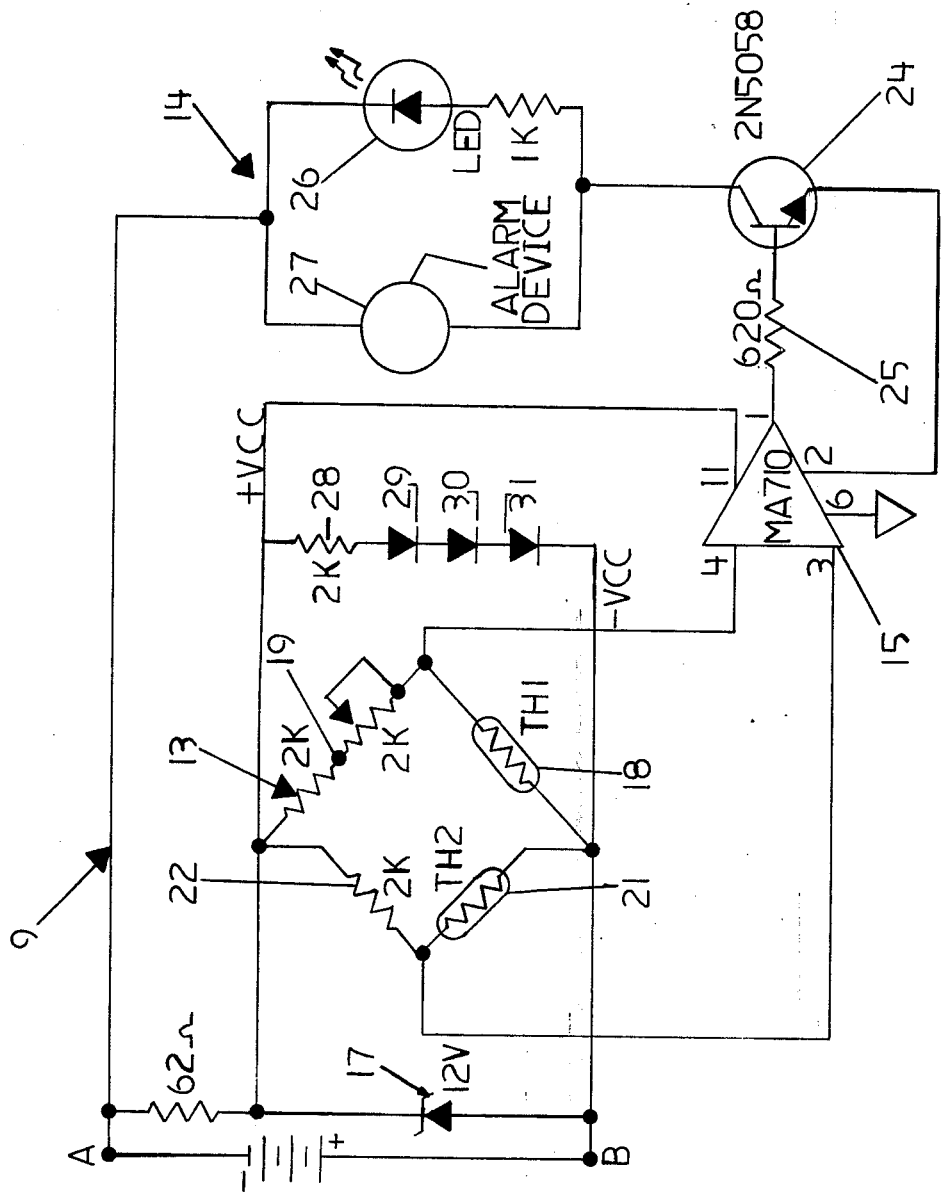

DESCRIPTION OF THE PREFERRED EMBODIMENT:

One type of detection circuit 9 which may be employed in the invention is shown in FIG. 1 for use with an A.C. line. Line wire current is fed through an iron core transformer 10 and to a rectifier bridge 11. The bridge feeds both ends of a detector bridge 13, and an audio alarm circuit 14; an operational amplifier 15 employed as a comparator is also fed by the rectifier bridge. A capacitor 16 filters the full wave regulated supply to produce a rippled voltage, and a Zener diode 17 provides voltage regulation. The bridge circuit employs a detector thermistor 18, an adjustable, 2K pot resistance 19, and a Zener diode 20; the resistance 19 is adjusted to set the Zener diode 20 about midway of the operating point of thermistor 18, which is about 300° K.–400° K. If desired, a thermistor 21 and resistance 22 can be substituted for the Zener diode and 700 ohm resistance 23. This embodiment is shown in FIG. 3. However, this is a more expensive circuit, and unlike the Zener diode, cannot be incorporated into an integrated circuit chip.

The Zener diode 20 is sensitive to small changes in thermistor outputs in the above mentioned temperature range, and hence, slight variations in this range will be detected by the Zener 20 when the bridge becomes unbalanced.

The comparator 15 is connected to the thermistor and Zener diode arms of the bridge. When the differential input to the op amp 15 is a few millivolts, it will change its state and turn on a transistor 24. The transistor is protected from overheating by a resistance 25. When the transistor is turned on, the circuit will be completed and the alarm circuit 14 will be activated to turn on an LED 26, audio alarm 27, a telemetry system, etc. Resistance 28 and diodes 29, 30 and 31 may be employed to reduce oscillations, etc.

The above arrangement, employing the rectifier bridge 11, is used for detection of overheating in a line wire due to an overload, to a defective appliance, to the line wire itself, etc. However, if the alarm circuit is used to monitor body temperature, a d.c. battery (dotted designation) can replace the transformer 10 and rectifier bridge 11 at contacts A, B.

If desired, the circuit components shown in FIG. 1 can be mounted on a board 30, shown in FIG. 2, which can be inserted between the plug and a receptacle. Alternatively, when worn by an individual, the circuit (except the LED, thermistor, audio, etc.) can be incorporated into an IC chip and secured by a tape, clip-on at the ear, etc. When used in conjunction with a line wire, the IC chip can be mounted at the end of an extension wire or any equipment line cord.

What is claimed is:

1. A detecting circuit for an overheated condition, comprising:
    (a.) a d.c. powered bridge circuit having a detector thermistor in a bridge arm, the bridge being fed by the d.c. source;
    (b.) thermistor response detector in an adjacent bridge arm, the detector being set for a response to thermistor changes in about the 300° K.–400° K. range;
    (c.) a two state comparator amplifier for activation by the thermistor response detector:
    (d.) an on-off switch activated by the amplifier; and,
    (e.) output signal means for the circuit connected to the on-off switch, whereby a bridge unbalance due to thermistor changes caused by an overload will activate the thermistor response detector, thereby activating the on-off switch and then turn on the output signal means.

2. The detecting circuit of claim 1 in which the comparator is an operational amplifier and the on-off switch is a transistor.

3. The circuit of claim 1, adapted for detection of an overheated body condition.

4. The circuit of claim 1 adapted for detection of an overheated line wire.

5. The circuit of claim 1, in which the thermistor response detector is a thermistor.

6. The circuit of claim 1, in which the detector is a Zener diode.

7. The apparatus of claim 1, comprising a plug board mounting for the circuit.

8. A method for signalling an overheated body condition, comprising:
    (a.) detecting skin temperature with a thermistor in one arm of a d.c. powered bridge circuit;
    (b.) providing a thermistor response detector in an adjacent opposing arm of the bridge circuit, the detector being set for a response to thermistor changes in the 300° K.–400° K. range;
    (c.) feeding bridge unbalance signals from the detector to a two state comparator amplifier;
    (d.) activating an on-off switch fed by the comparator when the bridge is unbalanced; and,
    (e.) turning on an output signal from the on-off switch, when the switch is activated.

9. The method of claim 6 in which the comparator is an operational amplifier and the on-off switch is a transistor.

10. The method of claim 8 in which a thermistor is the detector.

11. The method of claim 8, in which the detector is a Zener diode.

* * * * *